United States Patent [19]

Menaker, M.D.

[11] Patent Number: 5,207,706
[45] Date of Patent: May 4, 1993

[54] METHOD AND MEANS FOR GOLD-COATING IMPLANTABLE INTRAVASCULAR DEVICES

[76] Inventor: Gerald Menaker, M.D., 990 N. Lake Shore Dr., Chicago, Ill. 60611

[21] Appl. No.: 640,912

[22] Filed: Jan. 7, 1991

Related U.S. Application Data

[63] Continuation-in-part of Ser. No. 417,798, Oct. 4, 1989, abandoned, which is a continuation-in-part of Ser. No. 254,359, Oct. 5, 1988, abandoned.

[51] Int. Cl.$^5$ .................................. A61F 2/06
[52] U.S. Cl. .......................... 623/1; 623/12; 623/66; 604/266
[58] Field of Search .............. 623/1, 11, 12, 66; 427/2; 604/266

[56] References Cited

U.S. PATENT DOCUMENTS

| | | | |
|---|---|---|---|
| 3,094,762 | 6/1963 | Jeckel . | |
| 3,106,483 | 10/1963 | Kline . | |
| 3,572,343 | 3/1971 | Hirsch . | |
| 3,974,526 | 8/1976 | Dardik et al. . | |
| 3,988,782 | 11/1976 | Dardlik et al. . | |
| 4,054,139 | 10/1977 | Crossley | 623/66 |
| 4,073,999 | 2/1978 | Bryan et al. | 623/66 |
| 4,164,524 | 8/1979 | Ward et al. . | |
| 4,167,045 | 9/1979 | Sawyer | 623/1 |
| 4,229,838 | 10/1980 | Mono | 623/1 |
| 4,265,928 | 5/1981 | Braun . | |
| 4,275,469 | 6/1981 | Gabbay . | |
| 4,355,426 | 10/1982 | MacGregor . | |
| 4,557,957 | 12/1985 | Manniso . | |
| 4,569,673 | 2/1986 | Tesi . | |
| 4,676,975 | 6/1987 | McGary et al. . | |
| 4,678,660 | 7/1987 | McGary et al. . | |
| 4,693,721 | 9/1987 | Ducheyne . | |
| 4,704,131 | 11/1987 | Noishiki et al. . | |
| 4,718,907 | 1/1988 | Karwoski et al. . | |
| 4,720,400 | 1/1988 | Manniso . | |
| 4,743,253 | 5/1988 | Magladry | 623/2 |
| 4,871,366 | 10/1989 | von Kecum et al. | 623/11 |
| 4,877,030 | 10/1989 | Beck et al. | 128/343 |
| 5,034,265 | 7/1991 | Hoffman et al. | 604/266 |

OTHER PUBLICATIONS

The Use of Charged Gold Leaf in Surgery, Gallagher and Geschickter, JAMA, (1964).
Plasma Polymerized Tetrafluoroethylene/Polyethylene Terephthalate Vascular Prostheses, Greisler, Dennis et al, Aug. 1989.
Endothelial Seeding of Dacron and Polytetrafluoroethylene Grafts . . . , Herring et al., Surgery, 1984.
Antibiotic Bonding to Polytetrafluoroethylene with Tridodecylmethylammonium Chloride, Harvey et al, Surgery, 1982.
Complement Activation by Synthetic Vasular Prostheses, Shepard et al., Journal of Vascular Surgery, 1984.
Failure of Antiplatelet Therapy with Ibuprofen to Prevent Neointimal Fibrous Hyperplasia, McGready, et al., Journal of Vascular Surgery, 1985.
Endothelium develops on seeded human arterial prosthesis, Herring, et al., Journal of Vascular Surgery, 1985.
Use of Gore Tex E-PTFE Bonded to Silicone Rubber as an Alloplastic Implant. Berman, Laryngoscope, 1986.
Does Indium Platelet Deposition Predict Patency in Prosthetic Arterial Grafts Hall et al., Br. J. Surg. 1983.
Femoropopliteal Bypass Grafts., Goldman et al., Br. J. Surg. 1982.
The Role of Synthetic Grafts in Femorotibial Bypass. Dardik. Surgical Rounds, 1989.
The Effect of Fibronectin Coating on Endothelial Cell Klinetics., Ramalanjaona, et al., Journal of Vascular Surgery, 1986.

(List continued on next page.)

Primary Examiner—Randall L. Green
Assistant Examiner—Paul Prebilic
Attorney, Agent, or Firm—Jerry A. Schulman

[57] ABSTRACT

Implantable vascular prostheses, formed of synthetic, woven fibers are coated with a thin layer of metallic gold sufficient to create a continuous coating over the surfaces of the fibers that come into contact with blood. The coating is applied by vapor deposition or sputtering to coat the fibers without blocking or bridging the interstices formed by the intersection of the fibers.

7 Claims, 2 Drawing Sheets

OTHER PUBLICATIONS

Evaluation of the Thrombogenic Poteitial of Three Types of Arterial Graft Hamlin et al., Br. J. Surg. 1978.

The Systemic Activation of Platelets by Dacron Grafts, Shoenfeld et al, Surgery, Gynecology & Obstetrics, vol. 166, May 1988, pp. 454–457.

Synthetic Vascular Graft Trials Start, Endothelialization Seen as Possible, Medical News and Perspectives. Platelet Arterial Synthetic Graft Interaction and its Modification, Callow et al, Archives of Surgery, 1982.

Prevention of Platelet Aggregation and Adherence to Prosthetic Vascular Grafts by Aspirin and Dipyridamole. Oblath et al., Surgery, 1978.

Experimental and Clinical Use of Polytetrafluoroethylene Vascular Grafts. Santiago–Delpin et al., American Journal of Surgery, 1980.

Expanded Polytetrafluoroethylene Vascular Prostheses Seeded With Enzymatically Derived and Cultured Canine Endothelial Cells. Graham et al., Surgery, 1982.

Prevention of Vascular Prosthetic Infection by a Benzalkonium Oxacillin Bonded Polytetrafluoroethylene Graft, Greco et al., Surgery, 1982.

"Combination Therapy With Gold and Hydroxychloroquinine in Rheumatoid Arthritis: a Prospective Randomized Placebo–Controlled Study" (Scott, et al.) (Br. J. Rheumatology 1989 Apr: 28(2); 128–33.

"Results of Upper Lip Loading in the Treatment of Lagophthalmos Caused by Facial Palsy" (Chapman, et al.) (Br J. Plastic Surgery 1988 Jul; 31(4): 369–72.

"The Correction of Seventh Nerve Palsy Lagophthalmos with Gold Lid Load" (Newman, et al.) (Ann Plastic Surgery 1988 Feb; 22(2): 142–5.

METHOD AND MEANS FOR GOLD-COATING IMPLANTABLE INTRAVASCULAR DEVICES

This is a continuation-in-part of application Ser. No. 417,798, filed Oct. 4, 1989, now abandoned, which is a continuation-in-part of application Ser. No. 254,359, filed Oct. 5, 1988, now abandoned.

The present invention relates generally to implantable artificial grafts, shunts, patches and valves and, more particularly, to methods and means for limiting the formation of thromboses after such grafts, shunts, patches or valves have been surgically implanted into a living recipient.

BACKGROUND OF INVENTION

Surgical repair or replacement of major blood vessels or heart valves damaged by disease or injury is a difficult and delicate process. Where the blood vessel or valve involved has been damaged or has deteriorated to the point where it cannot be repaired, it must be replaced.

With respect to blood vessels, techniques have been developed to use arteries or veins from other parts of the patient's body, or from a donor, to substitute for the damaged or diseased body part. This results in a duality of required surgical procedures wherein a length of vessel suitable for replacing the injured or diseased portion is removed from one part of the body, or from the donor, and implanted at the site of the injury or disease.

The use of blood vessels from donors has been successfully carried out, but such procedures call for the suppression of the body's normal immune system antagonism toward the presence of foreign tissue. Although this procedure has become safer and more readily regulated, it requires drugs which may have untoward side effects on the patient. Certainly, the simpler and more straightforward a surgical procedure, the greater the likelihood that the patient will tolerate it well and will make a satisfactory recovery.

More recently, artificial shunts, grafts, patches and heart valves have been developed to be surgically implanted to replace those found to be damaged or defective. Such artificial expedients have been made from materials selected for their capacity to be tolerated well by the human body, to handle the requirements of fluid pressures demanded of the affected blood vessel or valve, and to provide attachment sites for the anchoring of sutures and the formation of scar tissue. Among such materials are tetrafluoroethylene (sold under the registered trademark "Teflon") and polyethylene glycol terephthalate (sold under the registered trademark "Dacron"). Both are especially well-suited for producing knitted, woven or braided implants grafts, or attachment cuffs. Another material so used for shunts, grafts and patches is an expanded microporous polytetrafluoroethylene sold under the registered trademark "Gore-Tex".

Examples of such an artificial heart valve are the valve manufactured by St. Jude Medical and Edwards CVS Division of Baxter Healthcare, Inc. The Edwards valve assembly consists generally of a rigid, rounded metallic valve body or frame within which a metallic valve plate or leaflet is rotatably suspended. A cuff or attachment ring fashioned from one of the materials described above surrounds the valve frame and provides an attachment site for fibrous tissue to infiltrate and anchor the valve assembly in place. The valve plate is shaped and pivoted to act as a check valve against the backflow of blood, and is thus in intimate contact with the stream of blood passing to or from the heart. A similar construction is utilized in the heart valve sold under the St. Jude Medical registered trademark. This valve utilizes a pair of leaflets as the blood flows regulators.

Examples of vascular shunts are shown and described in U.S. Pat. Nos. 4,167,045 (Sawyer) and 4,712,551 (Rayhanabad). Sawyer teaches a vascular shunt made from Dacron (Registered U.S. Trademark), coated with glutaraldehyde-polymerized proteins, aluminum or other substances. Sawyer also teaches that early attempts to use rigid, gold tubes as vascular shunts were unsuccessful.

Rayhanabad shows a multi-branched vascular shunt for temporary use during surgery. The use of such a shunt enables blood flow to be continued to vital organs even while a main blood vessel is being treated. For permanent implants, it is desirable to utilize a porous material for the shunt or graft to allow for the infiltration of the Pores by body tissue in order to firmly hold the shunt or graft in position and to create a shunt "formed" from living tissue. This need is balanced by the need to provide a liquid-tight conduit to operate as a replacement blood vessel. One approach to balancing these two needs is shown in U.S. Pat. No. 3,106,483 (Kline et al.), which acknowledges the prior use of artificial blood vessels formed by knitting, weaving or braiding polymer synthetic filaments such as "Dacron" (Registered U.S. Trademark) or "Teflon" (Registered U.S. Trademark). Use of knitted, woven, or braided implants is said to offer advantages in providing a porous surface into which body tissue may grow after implantation; such implants also offer a secure underlay for suturing. Kline et al. teach the use of an assimilatable coating within the graft which initially creates a liquid-tight conduit; the lining thereafter gradually dissolves into the blood stream leaving behind a porous network which by this time has been infiltrated and filled by body tissue to fill the pores and provide a liquid-tight vessel.

U.S. Pat. No. 3,094,762 (Jeckel) teaches the use of Teflon (Registered U.S. Trademark) knitted or woven into a blood vessel graft. Dardik et al., in U.S. Pat. No. 3,974,526, teach the use of the human umbilical cord as a vascular grafting material, including shaping and hardening the cord on a mandrel, chemically treating the umbilical cord to limit antigenicity, and using a reinforcing mesh to strengthen the resulting prosthesis.

The presence of thromboses or blood clots is of significant concern in any surgical procedure, and is also a most serious problem in using arterial-venous shunts or artificial heart valves. Clotting frequently occurs in dialysis shunts, requiring removal of the shunt, clearing and surgical reimplantation. The formation and dislodging of a clot may result in the occlusion or blocking of a blood vessel, interrupting the life-giving flow of blood to major organs of the body. Formation of thromboses in surgically implanted arterial or venous grafts may result because of such factors as the woven, porous nature of the graft material a construction which may attract blood platelets or debris in the blood stream. The graft's chemical composition, its compliance, and/or its electro-negativity, each of which may evoke a different tissue reaction may also contribute to thrombosis. See, for example, Greisler, et al., "Plasma Polymerized Tetrafluoroethylene/Polyethylene Terephthalate Vascular Prostheses", Arch. Surg., Vol. 124, pp. 967-972 (August, 1989). This creates the attendant risk that once a mass of detritus reaches a significant weight and size, it may adhere to the wall of the blood vessel, progressively blocking the vessel, or it may be dislodged by the flow of blood through the blood vessel and will travel until it encounters a blood vessel having a diameter of less than that of the thrombus, causing a blockage.

Prevention of thromboses in implantable shunts has been addressed in U.S. Pat. No. 3,988,782 (Dardik et al.) wherein the use of "pre-clotted" or hardened lengths of human umbilical cord as homografts is taught. The anti-thrombogenic properties of such homografts is, according to the patent, a product of the hardening of the umbilical cord length used to manufacture the homograft.

U.S. Pat. No. 4,355,426 (McGregor) teaches the construction of a metallic porous vascular graft, which depends for its anti-thrombogenic properties upon the formation of a smooth coating of tissue created by the growth of nucleated cells from the blood stream over the porous surface and sub-surface of the graft.

Ward et al. (U.S. Pat. No. 4,164,524) teach the technique of evacuating gas nuclei trapped in the walls of blood-treatment devices to minimize the presence of cavities within which blood platelets may collect to begin the clotting process.

Other attempts at limiting the formation of thromboses have utilized coating materials applied to the grafts or shunts. U.S. Pat. No. 4,718,907 (Karwoski et al.) teaches the use of a fluorinated coating applied electrically to the surfaces of an interwoven fabric tube. Braun (U.S. Pat. No. 4,265,928) teaches an anti-thrombogenic catheter dependent for its non-clotting properties upon the deposition of a thin coating of an ethylene-acrylic acid copolymer to the interior surface of the catheter.

Yet another approach to limiting the formation of thromboses is to use an anti-clotting agent, such as heparin, in the blood stream of the patient. Use of heparin or any other anti-coagulant has the undesirable side effect of robbing the blood of its ability to clot in the event of a traumatic injury. Attempts have been made to localize the anti-clotting effect of heparin as, for example, in U.S. Pat. No. 4,704,131 (Noishiki et al.) who teach the formation of a heparinized collagen to be used as a material for constructing artificial grafts or shunts. Similarly, U.S. Pat. Nos. 4,676,975 and 4,678,660 (McGary et al.) teaches the manufacture of anti-thrombogenic thermoplastic incorporating an anti-thrombogenic agent such as heparin into a polymer. The anti-thrombogenic agent is thus dispersed throughout the material used to construct the graft.

It has long been known that the use of gold in surgical procedures is well-tolerated by the human body because gold is essentially chemically inert, meaning it does not react with such commonly available reagents as sulfur, oxygen, water and the like. Gold is also electrically conductive, a property which may aid in the dispersal of electrical currents that may promote thromboses.

Surgical uses of gold leaf are described in an article entitled "The Use of Charged Gold Leaf in Surgery" authored by Dr. John P. Gallagher and Dr. Charles F. Geschickter, and Published in the Journal of the American Medical Association on Sep. 21, 1964. Drs. Gallagher and Geschickter describe a process well known to all those who have used gold leaf in the painting of signs, namely, the use of a camel's hair brush to impart an electrical charge to the gold leaf and the subsequent application of the gold leaf to a desired surface. It was found that gold was assimilated by the body without adverse reactions and without apparently requiring the use of drugs to control reactions of the body's immune system.

The therapeutic properties of gold, together with the body's long-term tolerance to the presence of gold have been recognized by the medical profession.

For example, the use of gold in the treatment of rheumatoid arthritis is described by D. L. Scott et al. in an article entitled "Combination Therapy With Gold and Hydroxychloroquinine in Rheumatoid Arthritis: a Prospective, Randomized, Placebo-Controlled Study" (Br. J. Rheumatology 1989 Apr: 28(2); 128-33).

Gold has also been used in plastic surgery, demonstrating the long term tolerance of tissue for this metal. See, for example, P. Chapman, et al., "Results of Upper Lip Loading in the Treatment of Lagophthalmos Caused by Facial Palsy" (Br J. Plastic Surgery 1988 Jul; 31(4): 369-72); and A. R. Newman, et al., "The Correction of Seventh Nerve Palsy Lagophthalmos with Gold Lid Load" (Ann Plastic Surgery 1988 Feb; 22(2): 142-5.

U.S. Pat. No. 4,054,139 (Crossley) teaches the use of metals such as silver and gold used in catheters to prevent bacterial infection. Such metals are applied in small amounts throughout the material used to form the catheter but Crossley does not suggest the use of a continuous metal coating to present an anti-thrombotic surface for permanent implantation.

U.S. Pat. No. 4,743,253 (Magladry) teaches the application of gold to a metallic compression ring used in a suture ring assembly for heart valves. This is an application which does not address the particular problems of preventing the formation of thromboses on the metallic or rigid portions of the heart valve itself nor on the suture ring and the fabric used to form an anchoring site for the ring. The suture ring of Magladry is ductile and electrically conductive but must be covered by a fabric to form an anchoring site for suturing to the heart.

It may thus be seen that the characteristics required for the construction of a successfully implantable graft, shunt, patch or valve are the ability of the human body to tolerate the presence of the material from which the implant is formed, the provision of a somewhat porous construction to enable body tissue to infiltrate the implant, thus holding it firmly in place, the resistance of the implant to leaks, particularly where used in a blood vessel subjected to the pressure pulses created by the pumping of blood by the heart and the provision of a mechanism whereby the formation of thromboses within or upon the implant is limited. Such implant should, ideally, be capable of use without requiring anti-coagulant drugs or compounds and should utilize materials which are uniformly non-reactive with body fluid constituents or tissues.

In my experience, many replacement heart valves are manufactured from pyrolitic carbon, and use fabric cuffs (typically Dacron ® or Teflon ®) to surround the suturing ring for use as an attachment site for sutures and, eventually, for infiltration by fibrous tissue. To my knowledge, no valves are presently available which provide gold as a protective coating for the hard surfaces as well as the individual fabric fibers. Such a coating should also ideally be highly electrically conductive to decrease the preserve of electrical currents with a concomitant decrease in the tendency for unwanted cell deposition to occur.

Meeting these criteria is of paramount importance given the rapid development of artificial implantable organs and replacement devices such as heart valves and the like which come into intimate contact with a patient's blood stream. Implants which otherwise function perfectly as replacements for body parts will continue to be unsuitable if such replacements, by their construction, provide sites at which thromboses can form. As discussed above, it has also been learned that the presence of electrical charges and the like provide a breeding ground for the formation of thromboses, and the presence or strength of these currents should be limited or dissipated.

Heretofore, attempted solutions to these problems have focused upon the interreaction of blood constituents with the material from which the implants are formed.

BRIEF SUMMARY OF THE INVENTION

Vascular grafts, shunts, patches and heart valves are provided with a metallic coating which is chemically inert, readily deformable, hydrophobic, electrically conductive and non-reactive with body tissue or fluids.

In a first, preferred embodiment of the present invention, synthetic vascular shunts and patches are provided with gold coatings applied by vapor-deposition or by sputtering. The use of the vapor-deposition technique is described in U.S. Pat. No. 4,167,045 (Sawyer) and in articles entitled "Vacuum Metallized Shielding" (distributed by Deep-Coat Metallizing, Inc. of Lemont, Illinois), and R. Allen Myers. "An Introduction to Functional Thin Films" presented at the June, 1987 EMI/RFI Symposium of Plastics Engineers. Sputtering is described in "The Handbook of Thin Film Technology" edited by Leon Maissel and Rheinhardt Glang (McGraw-Hill Publishing Co., 1970) at pages 3-30 through 3-37.

Such a coating should be capable of flexing with the implant as the implant is twisted into position for permanent attachment, as the implant may flex during pulsative transmission of blood therethrough. Such coating should also preserve the porous construction of the graft to allow for the infiltration of fibrous tissue.

In yet another preferred embodiment of the invention, artificial heart valves and the suturing cuffs used to anchor such valves are similarly coated with gold prior to implantation.

These and further aspects of the present invention will be more apparent upon a consideration of the accompanying drawings wherein.

DETAILED DESCRIPTION OF THE INVENTION

It is well-known that gold may be applied to a substrate or an article by the techniques of vapor-deposition or sputtering.

The present invention involves the construction of implantable, grafts, shunts, patches, heart valves or other devices to be incorporated as part of the vascular system of a living body consistent with the foregoing teachings of the prior art and providing the finished implants with a coating of gold. The coating is applied to the surfaces of the implant intended to come into contact with the patient's blood stream thereby providing a lining or coating which is chemically inert and which has been observed and predicted to inhibit the formation of thromboses and possibly infection.

A preferred embodiment of the present invention involves the manufacture of synthetic vascular grafts, shunts and cuffs from products such as Dacron (Registered U.S. Trademark), Teflon (Registered U.S. Trademark) or Gore-Tex (Registered U.S. Trademark) materials, and the subsequent application of a layer of gold thereto. It is expected that the layer of gold may be applied either during or after the manufacturing process, depending upon the specific manufacturing steps undertaken by the producer of such implants. For example, for implants formed by "rolling" a cylinder from a flat piece of synthetic material, it is expected that gold may be applied to the material before or after such rolling occurs. Where material is drawn, as over a mandrel, to form a seamless tube, it is expected that the vapor deposition or sputtering techniques will induce the gold to adhere tightly to the inner and outer walls of the implant.

Figure 1:
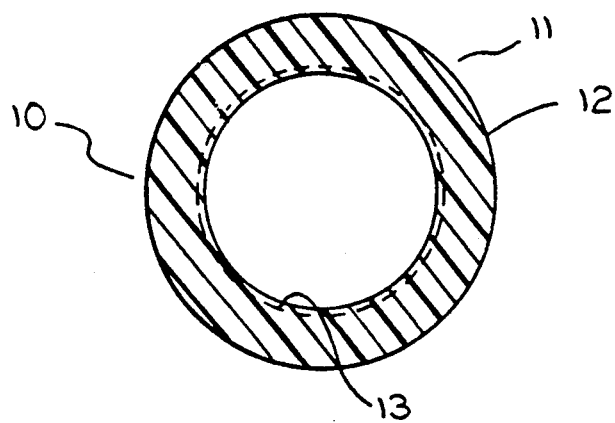
FIG. 1 is a sectional view of a portion of an implant in the form of a vascular shunt or graft embodying the present invention.
Figure 3:
FIG. 3 is a scanning electron microscope photograph taken at 15 KU #20× magnification showing vapor-deposition coating of a Dacron (Registered U.S. Trademark) implant.
Figure 4:
FIG. 4 shows the shunt of FIG. 3 at 15 KU 86× magnification.

In a first, preferred embodiment, a vascular shunt manufactured by Meadox Medicals, Inc. of Oakland, N.J. 07436 from Dacron (Registered U.S. Trademark) and sold under the trademark "Cooley 2" is coated with gold by the vapor-deposition process. As seen in FIG. 1, graft construction 10 includes a length of cylindrical shunt or graft 11 to which gold has been applied to outer wall 12 and inner wall 13 and the Dacron (Registered U.S. Trademark) construction is characterized by numerous interstices created by the woven nature of the fabric, as seen in FIGS. 3 and 4. It has been found desirable to maintain the openness of these interstices to provide sites for infiltration by fibrous body tissue. Such infiltration stabilizes and firmly holds the graft 11 after implantation. As shown in FIGS. 3 and 4, photomicrographic examination establishes that the individual fibers making up shunt 11 are coated evenly with gold without bridging or otherwise blocking the interstices formed by the weave pattern. It is expected that the gold so applied will penetrate within the intersticial fiber bundles so that the coating will extend inward from both the inner and outer surfaces.

The variety of vascular grafts manufactured by W. L. Gore and Associates use a fabric identified by the registered trademark Gore-Tex. The essential characteristic of Gore-Tex (Registered U.S. Trademark) fabric is a controllable and selectable distribution of pore sizes, making the material readily adaptable to create the type of pore distribution which will allow the implant to attract and support the growth of body tissue to hold the implant in place.

Another method of manufacture for graft 10 may be to vapor-deposit gold on an outer surface 14 of graft 11, then to turn graft 11 inside out to position gold layer 12 within shunt 11 along the path of blood flow.

Figure 2:
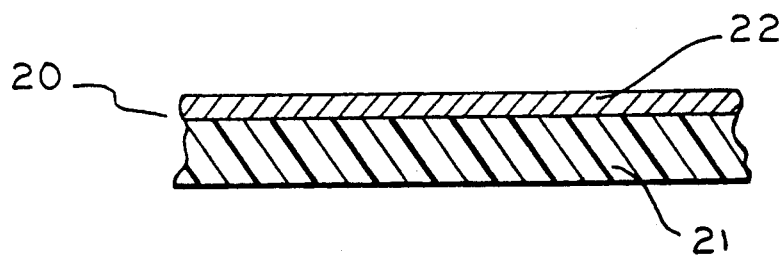
FIG. 2 is an implantable patch embodying the present invention.

Referring now to FIG. 2, the numeral 20 indicates generally a patch 21 prepared in accordance with the teachings of the present invention. A layer 22 of gold is applied to be coextensive with patch 21, and the patch may be trimmed to meet selected surgical requirements.

In the practice of a first, preferred embodiment of the invention, patch 20 has a coating 22 applied by vapor-deposition of metallic gold as described hereinabove.

Preferably, the use of gold with synthetic implants is contemplated. However, it is also expected that the techniques described herein are applicable to shunts such as those described in Dardik, et al. (U.S. Pat. Nos. 3,974,526 and 3,988,782).

Figure 5:
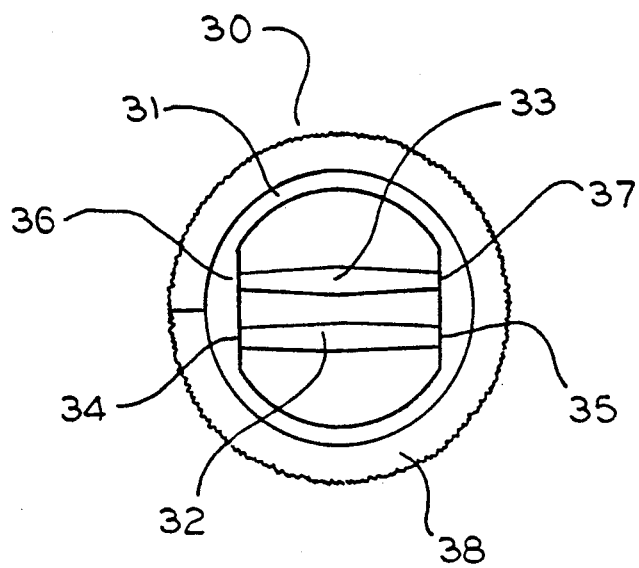
FIG. 5 shows a heart valve and suture cuff generally of the type discussed herein.

Referring now to FIG. 5, the numeral 30 indicates generally an artificial implantable heart valve. The particular valve herein depicted is one manufactured and sold under the registered trademark "St. Jude Medical", and consists of a generally circular valve housing 31 within which valve leaflets 32 and 33 are pivotally mounted. Leaflet 32 is supported at pivot points 34 and 35, while leaflet 33 is supported at pivot points 36 and 37. Leaflets 32 and 33 are shaped and suspended in such fashion as to pivot open when blood is pumped or drawn there through, and to pivot shut, preventing backflow, between heart beats.

When implanted, valve housing 31 is surrounded by suture cuff 38 formed, in one embodiment, from biocompatible Dacron® double velour vascular graft material. Cuff 38 is fashioned to eliminate seams along its outer surface to reduce the availability of sites for the generation of thromboses.

In the preferred practice of the present invention, valve 30 and cuff 38 are coated with gold by vacuum-deposition. Coating valve 30 provides the benefits described above with respect to prevention of thromboses, limiting of electrical currents, inertness and bio-compatibility. Gold coatings also help keep leaflets 32 and 33, and pivot points 34, 35, 36 and 37 clear of tissue and detritus to assure the reliable operation of the valve. It is also expected that the bacteriacidal properties of gold will aid in preventing or alleviating bacterial infections at the implant site.

Coating suture cuff 38 with gold provides these same benefits and preserves the presence of open interstices for the infiltration of fibrous tissue that will eventually anchor the cuff 30 and valve housing 31 into permanent contact with the heart tissue.

The use of the terms "vacuum deposition" or "sputtering" are not intended to be limiting, but to include other application techniques which allow devices such as those described herein to be protected by a coating of metallic gold while meeting the requirements of the present invention.

The present invention has been described in terms consistent with the implantation of artificial grafts, shunts, patches and valves in human beings, but it should be understood that the present invention may also be used in other animals as well.

While the foregoing has presented certain specific embodiments of the present invention, it is to be understood that these embodiments have been presented by way of example only. It is expected that others skilled in the art will perceive variations which, while differing from the foregoing, do not depart from the spirit and scope of the invention as herein described and claimed and no limitation as to the description of the present invention is hereby made or intended.

What is claimed is:

1. In a vascular graft for implanting into the blood circulatory system of a living recipient, said graft formed from a woven fabric of 'synthetic' material polymeric substrate, said fabric characterized by interstices created by the woven nature of the fabric another, said graft having a surface formed by said fabric, said surface for exposure to the blood of said recipient, the improvement comprising:

a thin layer of metallic gold applied to coat said fabric forming said surface, said layer applied to leave said interstices open and unblocked.

2. The construction of claim 1 wherein said vascular graft further comprises a tubular body formed from said fabric, said tubular body having an inner wall, said inner wall coated with gold.

3. The construction of claim 1 wherein said layer of metallic gold is vapor-deposited onto said vascular graft.

4. The construction of claim 1 wherein said layer of metallic gold i sputtered onto said vascular graft.

5. The construction of claim 1 wherein said synthetic material is tetrafluoroethylene polymer.

6. The construction of claim 1 wherein said synthetic material is polyethylene glycol terephthalate.

7. The construction of claim 1 wherein said synthetic material is expanded microporous polytetrafluoroethylene.

* * * * *